United States Patent
Wolf et al.

[11] Patent Number: 6,130,327
[45] Date of Patent: *Oct. 10, 2000

[54] REGENERATED CELLULOSE INCORPORATING PHOSPHORUS COMPOUNDS SO AS TO BE FLAME-RETARDANT

[75] Inventors: Rainer Wolf, Allschwil, Switzerland; Hartmut Rüf, Vöcklabruck, Austria

[73] Assignee: Lenzing Aktiengeselleschaft, Lenzing, Austria

[ * ] Notice: This patent issued on a continued prosecution application filed under 37 CFR 1.53(d), and is subject to the twenty year patent term provisions of 35 U.S.C. 154(a)(2).

[21] Appl. No.: 08/973,611
[22] PCT Filed: Jul. 4, 1996
[86] PCT No.: PCT/EP96/02945
  § 371 Date: Mar. 23, 1998
  § 102(e) Date: Mar. 23, 1998
[87] PCT Pub. No.: WO97/02315
  PCT Pub. Date: Jan. 23, 1997

[30] Foreign Application Priority Data

Jul. 5, 1995 [DE] Germany ............... 195 24 537

[51] Int. Cl.⁷ .................................................. C08B 16/00
[52] U.S. Cl. ............................................ 536/57; 536/124
[58] Field of Search ................. 536/57, 124; 514/54; 568/12, 15

[56] References Cited

U.S. PATENT DOCUMENTS

| 4,083,833 | 4/1978 | Siclari et al. | 260/79.3 |
| 4,855,507 | 8/1989 | Robertson et al. | 568/12 |

FOREIGN PATENT DOCUMENTS

| 9312173 | 6/1993 | WIPO . |
| 9421724 | 9/1994 | WIPO . |
| 9426962 | 11/1994 | WIPO . |

*Primary Examiner*—Elli Peselev
*Attorney, Agent, or Firm*—Baker Botts LLP

[57] ABSTRACT

The invention relates to flame-retardant regenerated celluloses which contain at least one compound of formula I:

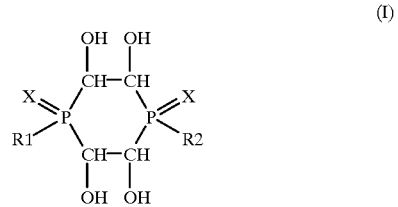

The subject matter of the invention is also the use of compounds of formula I as a flame-retardant agent especially for regenerated celluloses and a process for the flame-retardant finishing of regenerated cellulose which is characterized by mixing in compounds of formula I or a dispersion containing one of these compounds.

15 Claims, No Drawings

REGENERATED CELLULOSE INCORPORATING PHOSPHORUS COMPOUNDS SO AS TO BE FLAME-RETARDANT

BACKGROUND OF THE INVENTION

Regenerated celluloses, which contain selected phosphor compounds as a flame-retardant agent, constitute the subject matter of the invention.

SUMMARY OF THE INVENTION

The invention relates in particular to flame-retardant regenerated celluloses which contain at least one compound of formula I

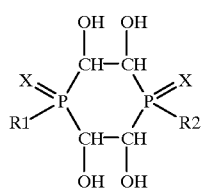

(I)

in which $R_1$, $R_2$ mean independently of each other an unsubstituted or substituted $C_{1-12}$ alkyl-, $C_{5-7}$ cycloalkyl-, $C_{7-12}$ aralkyl- or $C_{6-12}$ aryl-residue and X means oxygen or sulphur.

In formula I, $R_1$ and $R_2$ mean preferably an iso-butyl residue and X is preferably oxygen.

The compounds of formula I are well-known and can be manufactured in a manner known to the expert e.g. in accordance with the method described in U.S. Pat. No. 4,855,507.

The use of the above said components as flame-retardant agents in fully synthetic polymers, particularly polyolefines, impact-resistant modified polystyrenes, polyamide, polyphenylenoxide, polyphenylenoxides modified with impact-resistant modified polystyrenes, polyethylenetherephthalate and polyurethanes is likewise known. Surprisingly it was discovered that the compounds of formula I are also suitable for the flame-retardant finishing of regenerated cellulose. The subject matter of the invention is therefore also the use of compounds of formula I as a flame-retardant agent for regenerated cellulose and a process for the flame-retardant finishing of regenerated cellulose via the addition of compounds of formula I or dispersions containing these compounds.

DETAILED DESCRIPTION OF THE PREFERRED EMBODIMENTS

"Regenerated cellulose or cellulose hydrate" is a well-known expression. Regenerated cellulose is generally manufactured by bringing the cellulose into solution form using established processes. This is performed by dissolving the cellulose in suitable organic solvents such as amine oxides, particularly N-methyl morpholine oxide ("Lyocell process") or by converting the cellulose into soluble cellulose derivatives such as xanthogenate ("viscose process") or soluble tetramine-copper-(II)-hydroxide complexes ("Glanzstoff process"). The compound(s) of formula I are added as such to the cellulose solution or dispersed in a suitable medium. The addition is performed using well-known processes either continuously or discontinuously e.g. in batches, followed by rigorous mixing in order to distribute the compound(s) in formula I respectively a dispersion evenly in the cellulose solution. The regenerated cellulose is precipitated from the previously named solutions which contains the compound(s) of formula I using an established process e.g. by pressing this solution through fine nozzles or slits to manufacture filaments or films. The important technical properties of the regenerated cellulose are only slightly influenced by the addition of a flame-retardant agent of formula I according to the invention.

It is especially preferred that the flame retardant regenerated cellulose in accordance with the invention is precipitated from solutions of the cellulose in amine oxides, preferably N-Methylmorpholine oxide.

It is generally known, that cellulose can be very well dissolved in aqueous tertiary amine oxides, especially N-Methylmorpholineoxide (NMMO). The manufacture of cellulosic products from such solutions of cellulose in amine oxides is carried out in known manner by extruding the solution through a shaping tool and conducting the solution into an aqueous precipitation bath whilst stretching it, whereby the cellulose is precipitated from the solution.

It has been shown, that the compounds of formula (I) and especially the compound of formula (I), in which $R_1$ and $R_2$ mean iso-butyl and X means oxygen, are very stable against the conditions of this process in comparison with commercial products known in the state of the art. Thereby a flame retardant cellulosic product can be obtained in an economic manner.

The flame retardant cellulose can be present in the form of e.g. a fibre or a film depending on the shaping procedure.

Regenerated flame-retardant celluloses in accordance with the invention contain the compound(s) of formula I in quantities of 5–35 weight percentage, preferably 10–25 weight percentage and in particular 25 weight percentage related to 100 weight percentage of pure, regenerated cellulose. Corresponding amounts of the compound(s) of formula I are added to the cellulose solution before shaping.

In the case of the Lyocell-process, however, the compounds of formula (I) can also be added to an aqueous suspension of cellulose in tertiary amine oxides, which is used for making the solution.

The manufacture of dispersions in accordance with the invention is performed in well-known manner e.g. by grinding a concentrated mixture comprising a dispersion agent, a dispersion medium and compound(s) of formula I e.g. in a ball, sand, glass bead or quarzite mill until the size of the undissolved particles lies in the average of 0.5–5 µm, preferably 1 µm and if necessary by the adjustment of the desired concentration as a result of adding a dispersion medium which is preferably water.

In general the dispersions in accordance with the invention contain 10–60 weight percentage, preferably 15–50 weight percentage and in particular 20–40 weight percentage of a compound or a mixture of the compounds of formula I, 4–50 weight percentage, preferably 5–45 weight percentage and in particular 6–35 weight percentage of a dispersion agent, based on the weight of the compound(s) of formula I. The remainder is dispersion medium, preferably water.

In the following examples the parts mean weight parts and the percentages, if nothing else is indicated, weight percentages.

I. Manufacture of Dispersions in Accordance With Invention

EXAMPLE 1

A 25 percent aqueous dispersion of the compound of the following formula (1)

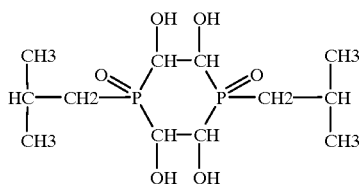

is manufactured as follows:

25 parts of a compound of formula 1 and 6.25 parts of a dispersion agent on the basis of sodium naphthalene sulphonate are mixed and stirred into 68.75 parts of water. The mixture is then ground in a ball mill of the type Dyno KDL pilot using 1100 ml Quarzite. Following the first passage through the mill, the mixture is ground for 68 hours in circuit. The dispersion is then filtered.

II. Manufacture of Regenerated Celluloses in Accordance With Invention

EXAMPLE 2

15 parts of a dispersion manufactured according to example 1 are added whilst mixing to 200 parts of a xanthate solution, which is manufactured from 18 parts of α-cellulose. This solution is pressed through the spinnerets of a conventional spinning device into a precipitation bath which contains 125 g of sulphuric acid ($H_2SO_4$), 240 g of anhydrous sodium sulphate ($Na_2SO_4$) and 12 g of anhydrous zinc sulphate ($ZnSO_4$) per liter. The fibres obtained in this manner are thoroughly washed, dried and processed to a knitted fabrics. These knitted fabrics are subjected to a flammability test using the method of Fenimore and Martin (Modern Plastics, November 1966) whereby the LOI value (oxygen limit value) is determined.

The comparison between the cellulose knitted fabrics made flame-retardant in accordance with the invention clearly shows reduced flammability as a result of the presence of compound (1):

LOI value of cellulose knitted fabric in accordance with the invention: 27

LOI value of untreated cellulose knitted fabrics: 19

EXAMPLE 3

An aqueous dispersion containing 10 weight percentage of the compound of formula (1) according to example 1 and 3 weight percentage of a tenside (Hypermer PS 2, Company: ICI), was ground in a bead mill, until no parts of the flame retardant compound larger than 5 μm could be found by microscopic assessment.

In a kneader of the type HKD-T 0.6 of company IKA-Labortechnik a spinning dope was produced from 233 g 50 percent aqueous NMMO, 14.5 g pulp (Buckeye V5) and 45 g of the above said dispersion by evaporation of excess water. The dope was composed of 9.0 weight percentage cellulose/3.0 weight percentage compound (1)/76 weight percentage NMMO/12 weight percentage $H_2O$.

As a spinning apparatus a melt index instrument of the company Davenport commonly used in plastic processing was used. The instrument is made of a heated cylinder able to be temperature-regulated, into which the spinning dope is filled. Using a piston, the propulsive force of which is controlled via an engine, the spinning dope is extruded through the spinneret attached to the lower side of the cylinder.

The dope was extruded through a one-hole/100 μm spinneret at a temperature of 100° C. and at an output of 0.025 g/hole/minute and the cellulose was precipitated after passing an air gap with a length of 60 mm in a water bath, temperature of 23° C. and length 20 cm.

The following fibres were obtained:
Methods

Textile examinations according to BISFA instruction "Internationally agreed methods for testing viscose, modal, cupro, lyocell, acetate and triacetate staple fibres and tows", edition 1993.
Amount of Phosphorus Digestion of the fibre with $H_2SO_4/H_2O_2$, photometrical measurement of the color reaction with ammonium molybdate.
Data for Example 3

| | |
|---|---|
| Titre (dtex) | 1,74 |
| Amount of phosphorus (%) | 3,98 |
| Fibre tenacity cond. (cN/tex) | 23,3 |
| Elongation at break cond. (%) | 9,4 |
| Fibre tenacity wet (cN/tex) | 18,0 |
| Elongation at break wet (%) | 11,9 |
| BISFA-Modul (cN/tex, 5%) | 7,4 |
| Loop strength (cN/tex) | 15,6 |
| Loop elongation (%) | 4,7 |
| Knot strength (cN/tex) | 20,6 |

The amount of phosphorus in the fibre resembles a yield of the incorporation of 86%. The difference to 100% contains material losses by flame retardant compound adhering to the glass beads of the grinding. The filament showed self-extinguishing behaviour when contacted with a flame.

EXAMPLE 4

An aqueous dispersion containing 10 weight percentage of the compound of formula (1) according to example 1 and 1 weight percentage of a tenside (Hypermer PS 2, Company: ICI), was ground in a bead mill, until no parts of the flame retardant compound larger than 5 μm could be found by microscopic assessment.

In a mixing vessel a spinning dope was produced from 3036 g 75 percent aqueous NMMO, 360 g pulp (Buckeye V5, Company Buckeye) and 900 of the above said dispersion by evaporation of excess water. The dope was composed of 12 weight percentage cellulose/3.0 weight percentage compound (1)/73.4 weight percentage NMMO/11.6 weight percentage $H_2O$.

The dope was extruded through a 200 hole/100 Mm spinneret at a temperature of 120° C. and at an output of 0.025 g/hole/minute, stretched in an air gap with a length of 30 mm and the cellulose was precipitated in a water bath. After washing out residual amounts of NMMO in the filament for 30 minutes the filament was dried at 70° C.

The following fibres were obtained:
Methods

Textile Examinations and amount of phosphorus according to example 3.
Determination of Limiting Oxygen Index (LOI)

20 g of a carded fleece are pressed at 180° C. and 200 bar for 1 hour to a test piece with an area weight of 76 g/m² and a thickness of 0.15 mm. This test piece was brought into a gas flow consisting of oxygen and nitrogen, whereby the amount of oxygen was increased stepwise. The LOI-Index means the oxygen concentration, at which the test piece just continues to burn after inflammation.

Data for Example 4

| Titre (dtex) | 1,55 |
|---|---|
| Amount of phosphorus (%) | 2,68 |
| Fibre tenacity cond. (cN/tex) | 35,6 |
| Elongation at break cond. (%) | 9,4 |
| Fibre tenacity wet (cN/tex) | 30,2 |
| Elongation at break wet (%) | 13,4 |
| BISFA-Modul (cN/tex, 5%) | 11,6 |
| Loop strength (cN/tex) | 14,0 |
| Loop elongation (%) | 1,9 |
| Knot strength (cN/tex) | 22,5 |
| LOI Index (%) | 24 |

What is claimed is:

1. Regenerated cellulose comprising at least one compound of formula I

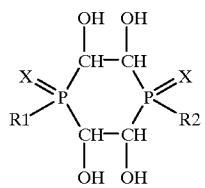

(I)

wherein $R_1$ and $R_2$ are independently selected from the group consisting of an unsubstituted $C_{1-12}$ alkyl-residue, an unsubstituted or substituted $C_{5-7}$ cycloalkyl-residue, an unsubstituted or substituted $C_{7-12}$ aralkyl-residue and an unsubstituted or substituted $C_{6-12}$ aryl-residue, wherein x is selected from the group consisting of oxygen and sulphur and wherein said regenerated cellulose is precipitated from a solution of cellulose comprising an amine oxide.

2. Regenerated cellulose in accordance with claim 1 wherein $R_1$ and $R_2$ are iso-$C_4H_9$ and x is oxygen.

3. Regenerated cellulose in accordance with claim 1 or claim 2 wherein the at least one compound of formula I is present in an amount of 5 to 35 weight percent relative to pure regenerated cellulose.

4. Regenerated cellulose in accordance with claim 1 or claim 2 wherein the cellulose is present in the form of one selected from the group consisting of a fibre and a film.

5. Process for the flame-retardant finishing of regenerated cellulose comprising the steps of:

providing a cellulose solution comprising an amine oxide, adding at least one compound of formula I in accordance with claim 1 to the cellulose solution, and precipitating regenerated cellulose from the cellulose solution wherein the at least one compound of formula I is added to the cellulose solution in the amount of 5 to 35 weight percent relative to pure regenerated cellulose.

6. Process in accordance with claim 5 wherein the at least one compound of formula I is added in the amount of 10 to 25 weight percent relative to pure regenerated cellulose.

7. Process according with claim 5 or claim 6 wherein the cellulose solution is shaped into one selected from the group consisting of fibres and films.

8. Dispersion for the flame-retardant finishing of regenerated cellulose comprising at least one compound of formula I in accordance with claim 1, a dispersing medium and at least one dispersion agent and optionally one selected from the group consisting of a dispersion stabilizing agent and a dispersion stabilizing mixture.

9. Dispersion according to claim 8 comprising 10 to 60 weight percent of the at least one compound of formula I and 4 to 50 weight percent of at least one dispersion agent relative to the weight of the at least one compound of formula 1.

10. Dispersion in accordance with claim 8 or claim 9 wherein the dispersing medium is water.

11. Regenerated cellulose in accordance with claim 3 wherein the at least one compound of formula I is present in an amount of 10 to 25 weight percent relative to pure regenerated cellulose.

12. Regenerated cellulose in accordance with claim 11 wherein the at least one compound of formula I is present in an amount of 25 weight percent relative to pure regenerated cellulose.

13. Regenerated cellulose in accordance with claim 1 or 2 wherein the cellulose is produced by precipitation from a solution of cellulose in N-methylmorpholinoxide.

14. Process according to claim 6 wherein the at least one compound of formula I is added in the amount of 25 weight percent relative to pure regenerated cellulose.

15. Process according to claim 6 wherein the cellulose solution comprises N-methylmorpholinoxide.

* * * * *

UNITED STATES PATENT AND TRADEMARK OFFICE
CERTIFICATE OF CORRECTION

PATENT NO.  : 6,130,327
DATED       : October 10, 2000
INVENTOR(S) : Wolf et al.

It is certified that error appears in the above-identified patent and that said Letters Patent is hereby corrected as shown below:

Title page, item [57],
ABSTRACT, formula (I), "R1" and "R2" should read -- $R_1$ -- and -- $R_2$ --

Column 5,
Formula (I), "R1" and "R2" should read -- $R_1$ -- and -- $R_2$ --
Line 35, "sulphur and" should read -- sulfur, and --
Line 39, "x" should read -- X --
Line 46, "fibre" should read -- fiber --

Column 6,
Line 16, "fibres" should read -- fibers --
Line 27, "1." should read -- I. --
Line 40, "N-methylmorpholinoxide" should read -- N-methylmorpholineoxide --
Line 45, "claim 6" should read -- claim 5 or 6 --
Line 46, "N-methylmorpholinoxide" should read -- N-methylmorpholineoxide --

Column 1,
Formula (I), "R1" and "R2" should read -- $R_1$ -- and -- $R_2$ --
Line 37, "polyolefines" should read -- polyolefins --
Line 39, "polyphenylenoxide," should read -- polyphenyleneoxide, --; and "polyphenylenoxides" should read -- polyphenyleneoxides --
Line 40, "polyethyleneth-" should read -- polyethylene- --
Line 41, "erephthalate" should read -- terephthalate --
Line 62, "tetramine-" should read -- tetraamine- --

Column 2,
Line 1, "a" should read -- in --
Line 3, "contains" should read -- contain --
Line 46, "quarzite" should read -- quartzite --

Column 3,
Formula (I), "CH2" (both occurrences) should read -- $CH_2$ -- and "CH3" (four occurrences) should read -- $CH_3$ --
Line 16, "Quarzite." should read -- quartzite. --
Line 32, "processed to a...etc."

Column 4,
Table, replace commas with decimal points
Line 49, "Mm" should read -- µm --

UNITED STATES PATENT AND TRADEMARK OFFICE
CERTIFICATE OF CORRECTION

PATENT NO. : 6,130,327
DATED : October 10, 2000
INVENTOR(S) : Wolf et al.

It is certified that error appears in the above-identified patent and that said Letters Patent is hereby corrected as shown below:

Column 5,
Table, replace commas with decimal points

Signed and Sealed this

Thirtieth Day of October, 2001

Attest:

NICHOLAS P. GODICI
Attesting Officer    Acting Director of the United States Patent and Trademark Office